United States Patent [19]

Tumerman

[11] 4,309,110
[45] Jan. 5, 1982

[54] METHOD AND APPARATUS FOR MEASURING THE QUANTITIES WHICH CHARACTERIZE THE OPTICAL PROPERTIES OF SUBSTANCES

[76] Inventor: Leo Tumerman, Melzer Str. 10, Apt. 4, Rehovoth, Israel

[21] Appl. No.: 28,817

[22] Filed: Apr. 10, 1979

[30] Foreign Application Priority Data

Apr. 23, 1978 [IL] Israel .................................. 54667

[51] Int. Cl.³ .............................................. G01J 4/00
[52] U.S. Cl. ..................................... 356/365; 356/366
[58] Field of Search ............... 356/366, 364, 327, 339, 356/435, 73, 365, 367, 368, 369, 370

[56] References Cited

U.S. PATENT DOCUMENTS

| 3,558,215 | 1/1971 | De Lang et al. | 350/150 |
| 3,724,952 | 4/1973 | Vossberg | 356/366 |
| 4,042,302 | 8/1977 | Wentz | 356/364 |

OTHER PUBLICATIONS

Danielsson et al., "Polarization Measurement on Spectral Lines of Low Intensity and Short Duration", Jour. Phys. E., vol. 7, 10-74, pp. 817-820.
Clarke et al., "Polarized Light and Optical Measurement", Pergamon Press, 1971, pp. 136-139.

Primary Examiner—Alfred E. Smith
Assistant Examiner—Carolyn E. Fields
Attorney, Agent, or Firm—Kenway & Jenney

[57] ABSTRACT

An apparatus and method for determining optical properties of a substance by passing a beam of linearly polarized light through the substance. The polarization vector of the light rotates at a definite frequency but the intensity does not depend upon the orientation of the vector. The relative phase shift and/or modulation coefficient of this beam is compared with a reference beam to effect measurements of light absorption, light scattering, linear and circular birefringency, and linear and circular dichroism, all of which can be measured separately or simultaneously by a single instrument.

14 Claims, 2 Drawing Figures

METHOD AND APPARATUS FOR MEASURING THE QUANTITIES WHICH CHARACTERIZE THE OPTICAL PROPERTIES OF SUBSTANCES

BACKGROUND OF THE INVENTION

Known in the prior art are various visual and photoelectric methods for measuring optical quantities. Known in the prior art also are many apparatuses for measuring the light absorption (spectrophotometers), light scattering (nephelometers), circular birefringency (spectropolarimeters) and circular dichroism (spectrodichrographs). With respect to the measurements of linear birefringency (double refraction) and linear dichroism, no instruments are now to our best knowledge produced on the commercial basis. There exist only some laboratory devices for these measurements built in scientific institutes where they are needed.

Physical principles underlying these methods and instruments are specific for the measured quantity. Therefore each of these instruments provides the possibility to measure only one of the aforementioned optical quantities. Different instruments are required to measure various quantities.

SUMMARY OF THE INVENTION

To overcome this disadvantage and to improve the accuracy and sensitivity of optical measuring devices we propose:

1.—A new method for measuring all or any of the aforementioned optical quantities which differs from the existing ones by the following main singularities:

a. A beam of linearly polarized light is used in all kinds of measurements, whose direction of polarization rotates with a definite frequency, but the intensity of which does not depend upon the orientation of the polarization vector.

b. The values of all the aforementioned optical quantities are computed from the measured value of the phase or the modulation coefficient of the alternating electric signal generated in the photodetector, e.g. a photomultiplier, by the said beam of light passing through the substance under investigation and through an analyzer or an achromatic quarter wave retardating plate which can be presented by a duly set Babinet-Soleil Compensator.

2.—An apparatus for measuring all or any of the aforementioned optical quantities which is based on the proposed method and contains as its essential parts:

a. A light source and a monochromator b. A device to transform the monochromatic beam of light emerging from the monochromator into a beam of linearly polarized light whose polarization direction rotates with a definite frequency, but the intensity of which does not depend upon the orientation of the polarization vector.

c. Devices to split the said beam of light with rotating polarization direction into two partial beams with the same properties and to focus both these partial beams on the same place of a photodetector, e.g. a photomultiplier.

d. Analyzers in both the said partial beams of light whose transmission directions are turned on an angle of 45° with each other.

Devices to rotate said analyzers to effect changes in said transmission direction. Devices to rotate the sample under investigation to effect changes in the transmission direction of the beam after it has passed through said sample.

e. An achromatic quarter wave retardating plate or a duly set Babinet-Soleil Compensator which can replace the analyzer in one of the said partial beams of light.

f. Devices to measure the phase and/or the modulation coefficient of the electric signal generated in the photodetector by the light transmitted by the substance under investigation.

The general idea of the proposed method and instrument is to replace the measurements of the resulting signal intensity as is typically done in the art by the measurements of its phase and/or of its modulation coefficient.

DESCRIPTION OF INVENTION

System Diagram

The invention will now be explained with reference to a particular embodiment thereof and the appended drawings.

Figure 1:
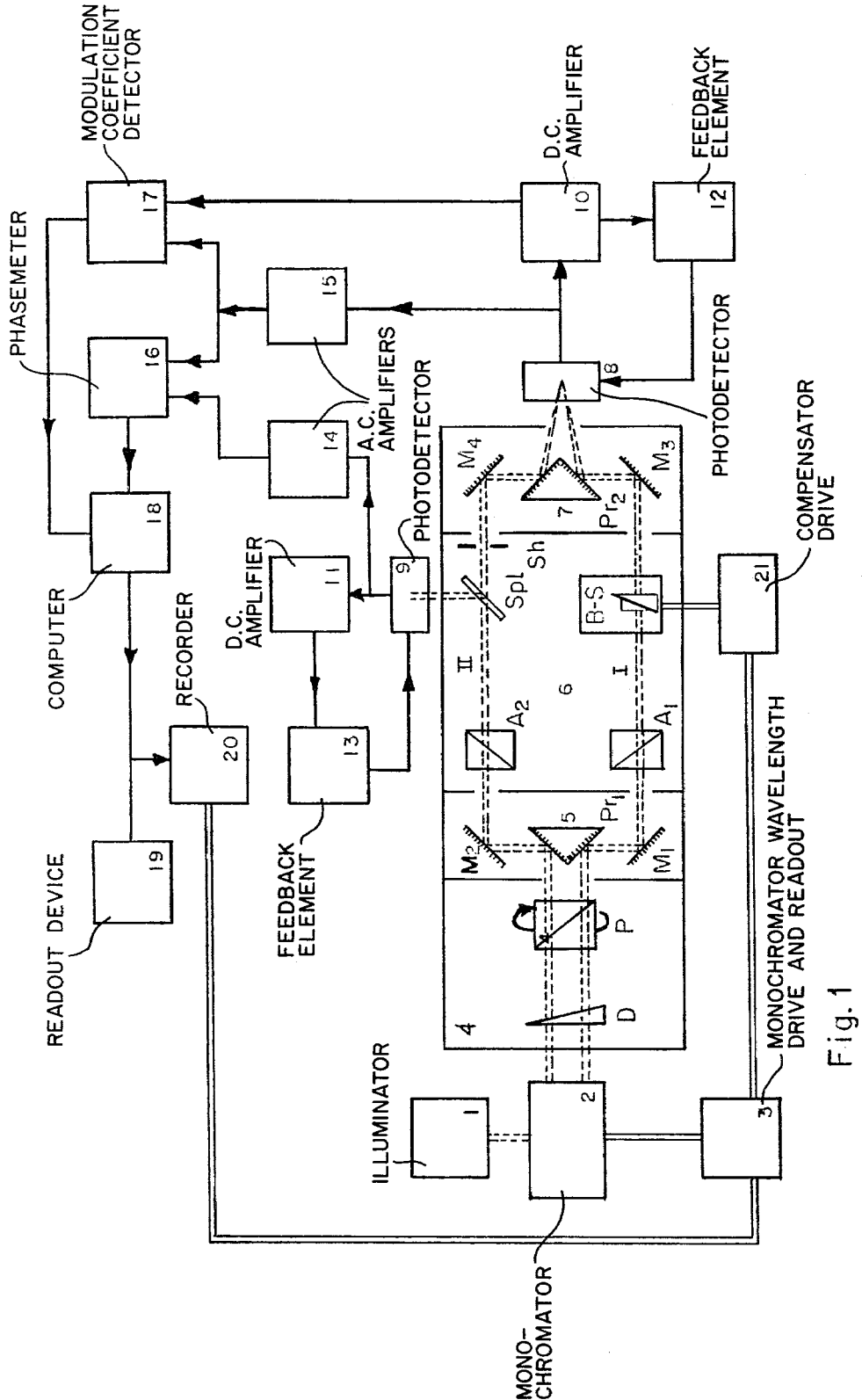
FIG. 1 is a system diagram of the apparatus according to the invention.

FIG. 1 is the system diagram, wherein:

1—is an illuminator, which contains the light source and the optical system focusing the light on the entrance slit of a monochromator;

2—is the monochromator;

3—is the monochromator's wavelength drive and readout;

4—is a device to transform the light emerging from the monochromator into the linearly polarized light with the rotating polarization direction, the intensity of which does not depend upon the orientation of the polarization vector;

5—is a device to split the said beam of light into two partial beams with the same polarization properties;

6—is the sample compartment;

7—is a device to focus both the said partial beams of light on the same place of the photodetector's sensitive area;

8 and 9—are photodetectors, e.g. photomultipliers;

10 and 11—are DC amplifiers;

12 and 13—are feedback devices which make the intensity of the signal generated in the detector independent upon the intensity of light producing the signal;

14 and 15—are AC multipliers;

16—is a phasemeter;

17—is a device to measure the modulation coefficient of the resulting signal, i.e. the ratio of the signal's alternating component amplitude to the direct component;

18—is a computer programmed to compute the values of the measured optical quantities from the measured value of the signal's phase or modulation coefficient;

19—is the readout of results;

20—is the recorder;

21—is the Babinet-Soleil Compensator's drive connected to the monochromator's drive.

Optical components

D—depolarizer, e.g. a 1° quartz prism cut parallel to the crystal's optical axis;

P, $A_1$ and $A_2$—polarizers, e.g. polarizing prisms $M_1$–$M_4$—mirrors;

$Pr_1$ and $Pr_2$—rectangular prisms with reflecting faces;

BS—Babinet-Soleil's Compensator;

Spl—beamsplitter;

Sh—shutter.

Light beams: = = = = = = =

Electrical connections: ─────────

Mechanical connections: ══════════

Figure 2:
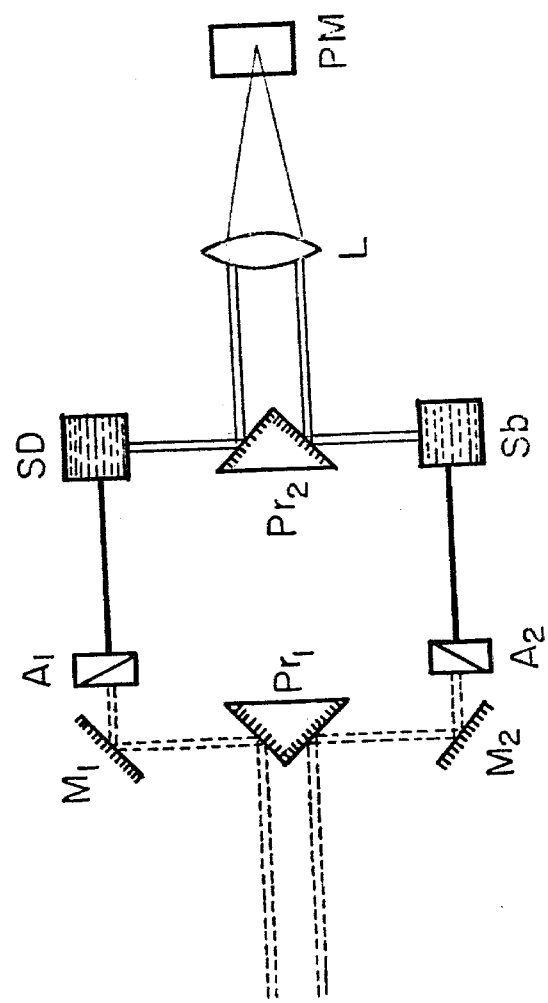
FIG. 2 is a schematic presentation of an arrangement for measuring the scattering coefficients of a substance.

FIG. 2 is a schematic presentation of a possible arrangement for measuring the scattering coefficients of a substance, wherein:

$Pr_1$ and $Pr_2$ are prisms with reflecting faces;

$M_1$ and $M_2$ are mirrors;

SD is a standard diffusor;

Sb is the substance under investigation;

L is a lens;

PM is a photodetector, e.g. a photomultiplier;

= = = = are beams of light with the rotating polarization direction;

───────── are beams of linearly polarized light;

═════════ are beams of light scattered by the standard diffusor or by a substance under investigation.

SYSTEM OPERATION

Light emitted by a suitable light source, e.g. a deuterium, mercury, xenon or halogen filament lamp, is focused by the illuminator 1 on the entrance slit of the monochromator 2 equipped as usual by the wavelength drive assembly 3 and by a wavelength readout. The monochromator can be replaced by or supplemented with suitable optical filters.

The monochromatic beam of light emerging from the monochromator is transformed by the device 4 into a beam of linearly polarized light, whose polarization direction rotates with a definite cyclic frequency $\omega$, but the intensity of which does not depend upon the orientation of the polarization vector. That can be done, e.g., by letting the light pass first through a depolarizer D, e.g. a crystalline quartz 1° prism cut parallel to the quartz optical axis, and then through a rotating polarizer P, e.g. a polarizing prism or a polaroid. Alternatively one could replace the depolarizer D by a fixed polarizer and the rotating polarizer by a known device to rotate the direction of the linearly polarized light.

The device 5 splits the said beam of light with the rotating polarization direction into two partial beams with the same polarization properties. That can be done, e.g., by the rectangular prism $Pr_1$ with reflecting (metallized) faces and by two mirrors $M_1$ and $M_2$, as it is shown on FIG. 1. Both these partial beams of light pass through the sample compartment 6 and are focused by the device 7 similar to the device 5 on the same place of the photosensitive area of a photodetector 8.

One of these beams (beam I on the FIG. 1) passes through the analyzer $A_1$ which can be replaced by the Babinet-Soleil compensator or the achromatic quarter-wave plate in the case of the circular dichroism measurements.

Depending on the characteristic being measured, the sample of substance under investigation is placed into this beam of light either before or after the analyzer, or, in the case of circular dichroism measurements, after the compensator.

The second partial beam of light (beam II on the FIG. 1) passes through the analyzer $A_2$ whose transmission direction makes an angle of 45° with that of the analyzer $A_1$. A part of the light transmitted by the analyzer $A_2$ is reflected by the beamsplitter Spl to the "reference" photodetector, e.g. a photomultiplier, 9. The beam II can be shut off by the shutter Sh after a part of it has been reflected to the detector 9.

The analyzers $A_1$ and $A_2$ transform the incident light with the rotating polarization direction into a light with a fixed polarization direction whose intensity is proportional to $(1+\cos 2\omega t)$. The direct components of the electric signals generated in the detectors 8 and 9 by the said beams of light are amplified by DC amplifiers 10 and 11 and are stabilized by the feedback devices 12 and 13 which control, e.g., the dynode voltage of multipliers 8 and 9 and make the intensity of the signal independent upon the intensity of light acting on the detectors. The alternating parts of the said signals are amplified by the AC amplifiers 14 and 15 and fed to the inputs of the phasemeter 16 which measures the phase difference between them.

The device 17 measures the ratio of the amplitude of the alternating part of the signal generated in 8 to its direct part, i.e. the modulation coefficient of the said signal.

The measured values of the signal's phase or modulation coefficient are transferred to a minicomputer 18 which computes the values of the measured optical quantity as it will be described later. The results are read on the digital readout 19 and/or recorded in analogous form by the recorder 20. Alternatively they can be recorded in the digital form by a printer or by any one of known devices, e.g. on magnetic tape or on punch cards.

SYSTEM FUNCTIONING

Let us see now how the measurements of all the aforementioned optical quantities can be carried out by the proposed method and by the instrument presented schematically on FIG. 1 and hereinbefore described.

I. Measurements of light absorption

The absorption of light by a substance is characterized usually by the substance's transmittency $T=J:J_o$ or by its absorbency (optical density) $A=-\log T$ (here $J$ and $J_o$ are the values of the intensity of light falling onto the substance and transmitted by it respectively).

To measure the quantities T and A by the proposed method and instrument, i.e. to use the instrument as a spectrophotometer, we have:

a. To place the substance under investigation, e.g. the solution, into one of beams of light I or II on the FIG. 1 and the reference substance, e.g. the solvent, into the other beam, both samples being placed after the corresponding analyzers.

b. To measure the phase of the resulting signal produced in the photodetector 8 by the simultaneous action of both the said beams of light against the signal produced in the detector 9 by the reflected part of the beam II.

Since the analyzers $A_1$ and $A_2$ are oriented at an angle of 45° with each other, the alternating parts of the electric signals produced by them are shifted in phase at an angle of 90°. It is easy to see now that the quantities T and A can be computed from the measured values of the said phase difference $\phi$:

$$T = \frac{\tan \phi_1}{\tan \phi_o} \; ; \; A = \log tg \, \phi_o - \log \tan \phi_1 \quad (1a)$$

or $$T = \left[\frac{\tan \phi_1}{\tan \phi_2}\right]^{\frac{1}{2}} ; \; A = \frac{\log \tan \phi_2 - \log \tan \phi_1}{2} \quad (1b)$$

where $\phi_o$ is the phase difference measured in the absence of substances in both beams of light or in the presence of the same substance in both of them; $\phi_1$ is the phase difference measured in the presence of the substance under investigation in the beam I and of the reference substance in the beam II; $\phi_2$ is the phase difference measured with the substance under investigation being placed into the beam II and the reference substance into the beam I.

2. Measurements of the circular birefringency (optical rotation)

The circular birefringency (optical rotation) of a substance is characterized usually by the angle $\alpha$ on which the polarization plane of the incident linearly polarized light is turned by passing through the substance.

To measure this angle by the proposed method and instrument, i.e. to use the instrument as a spectropolarimeter, we have:

a. To place the substance under investigation into the beam I on the FIG. 1 before the analyzer $A_1$ and to close the shutter in the second beam II.

b. To measure the phase of the resulting electric signal generated in the detector 8 by the light passing first through the substance and then through the analyzer against the signal generated in the detector 9 by the reflected part of the beam II.

If $\phi_s$ and $\phi_o$ are the values of the said phase difference measured in the presence and absence of the substance under investigation in the light beam I, then obviously $$\alpha = (\phi_s - \phi_o)/2 \quad (2)$$

The sign of the difference $(\phi_s - \phi_o)$ determines the direction of optical rotation.

3. Measurements of the linear birefringency (double refraction)

The linear birefringency (or the double refraction) of a substance is characterized usually by the difference of its two "principal" refraction indices $n_o$ and $n_e$ which correspond to the ordinary and extraordinary ray respectively.

To simplify the calculations we assume that the substance under investigation is presented as a plane parallel plate whose surface is parallel to the substance's optical axis and is orthogonal to the direction of the incident beam of light with rotating polarization plane. Since the lightwaves polarized parallel and orthogonal to the optical axis propagate in a birefringent substance with different velocities, they leave the plate with a definite phase difference $\delta$. In other words the linearly polarized light is transformed by passing through the substance into a light polarized elliptically.

The phase difference $\delta$ introduced by the plate is connected to the difference $\Delta n = n_o - n_e$ by the simple relationship:

$$\delta = (2\pi l/\lambda) \cdot \Delta n \quad (3a)$$

where $l$ is the thickness of the plate and $\lambda$ the wavelength of the light in air.

In the proposed method and apparatus $\delta$ is measured directly and $\Delta n$ can be computed from (3a). To measure $\delta$ we have:

a. To place the sample of the substance into the beam of light I (FIG. 1) before the analyzer and to close the shutter in the second beam II.

b. To measure the phase difference $\phi$ between the electric signal generated in the detector 8 by the light beam I passing first through the substance under investigation and then through the analyzer $A_1$ against the reference signal generated in the detector 9 by the reflected part of the beam II.

To show how the phase difference $\delta$ between the light waves can be computed from the measured phase difference $\phi$ between the said electrical signals we shall describe the light beams by the four dimensional Stokes vector: [J; $P_1$; $P_2$; $P_3$] whose first component is the beam's intensity and the other three components describe its state of polarization. The action of an optical medium, e.g. a birefringent plate or a polarizer, on the light passing through this substance can be described by a suitable Müller's matrix. One can find the Stokes vector for the light transmitted by the medium by multiplying the Stokes vector of the incident light by the corresponding Müller's matrix.

We choose the transmission direction of the analyzer $A_1$ as the OX-axis of the system of coordinates in the plane orthogonal to the light beam I. Then the Müller's matrix for the polarizer $A_1$ is:

$$|P_o| = \begin{vmatrix} 1 & 1 & 0 & 0 \\ 1 & 1 & 0 & 0 \\ 0 & 0 & 0 & 0 \\ 0 & 0 & 0 & 0 \end{vmatrix}$$

The Müller's matrix for our birefringent plate is $|B_a| =$ $$\begin{vmatrix} 1 & 0 & 0 & 0 \\ 0 & \cos^2 2\alpha + \sin^2 2\alpha \cos \delta & \sin 2\alpha \cos 2\alpha (1 - \cos \delta) & -\sin 2\alpha \sin \delta \\ 0 & \sin 2\alpha \cos 2\alpha (1 - \cos \delta) & \sin^2 2\alpha + \cos^2 2\alpha \cos \delta & \cos 2\alpha \sin \delta \\ 0 & \sin 2\alpha \sin \delta & -\cos 2\alpha \sin \delta & \cos \delta \end{vmatrix}$$

where $\alpha$ is the angle the direction of fast oscillations of the substance makes with the OX-axis. (See, e.g., Walker, M. I., Matrix calculus and the Stokes parameters of polarized radiation, Amer. J. Phys., vol. 22, p. 170, 1954 or McMaster, W. H., Matrix representation of polarization, Rev. mod. Phys., vol. 33, p. 8, 1961).

If we assume that the polarization direction of the incident beam of light with rotating polarization plane is parallel to the OX-axis at the moment $t=0$, then the Stokes vector for the incident beam of light is:

$$\begin{vmatrix} J \\ P_1 \\ P_2 \\ P_3 \end{vmatrix} = \begin{vmatrix} 1 \\ \cos 2\omega t \\ \sin 2\omega t \\ 0 \end{vmatrix}$$

The Stokes vector for the light beam which acts on the photodetector 8 is therefore:

$$\begin{vmatrix} J \\ P_1 \\ P_2 \\ P_3 \end{vmatrix} = |P_o| \cdot |B_\alpha| \cdot \begin{vmatrix} 1 \\ \cos 2\omega t \\ \sin 2\omega t \\ 0 \end{vmatrix}$$

It is easy to show now by performing the multiplications that the intensity of the light acting on the detector 8 and therefore of the electric signal generated in this detector is proportional to $$J = 1 + M \cos(2\omega t - \psi)$$

where $$M^2 = [\cos^2 2\alpha t + \sin^2 2\alpha t \cdot \cos \delta)]^2 + [\sin^2 2\alpha \cos 2\alpha (1 - \cos \delta)]^2$$

and $$\tan \psi = \frac{\sin 2\alpha \cdot \cos 2\alpha (1 - \cos \delta)}{\cos^2 2\alpha + \sin^2 2\alpha \cdot \cos \delta} \quad (3b)$$

Since we measure the phase of the resulting signal against the signal generated in the detector 9 which is shifted on 90° relatively to the OX-axis, the measured phase difference $\phi = 90 - \psi$ and $$\tan \phi = \frac{\cos^2 2\alpha + \sin^2 2\alpha \cdot \cos \delta}{\sin 2\alpha \cdot \cos 2\alpha (1 - \cos \delta)} \quad (3c)$$

Obviously, $\phi = 90°$ independently of the value of $\delta$ at $\alpha = 0$, i.e. when the direction of fast oscillations in the plate is parallel to the transmission direction of the analyzer $A_1$. At any other orientation we can compute $\delta$ from the measured value of $\phi$ from (3c). The simplest way to do it is to make $2\alpha = 45°$. Then $$\tan \phi = \frac{1 + \cos \delta}{1 - \cos \delta} \quad (3d)$$

and $$\cos \delta = \frac{\tan \phi - 1}{\tan \phi + 1} \quad (3e)$$

Obviously, if the substance under investigation is both linearly and circularly birefringent, the values of both these quantities can be computed from the values of the signal's phase $\phi$ measured at $\alpha = 0°$ and at any other value of $\alpha$, preferably at $\alpha = 22.5°$.

Angle may be selected by rotation of either the polarizing analyzer or the substance under investigation.

4. Measurements of the circular dichroism

The circular dichroism of a substance is characterized usually by the difference of its molar absorption coefficients $\epsilon_d$ and $\epsilon_l$ for the right-hand and left-hand circular polarized light:

$$\Delta_c = \epsilon_d - \epsilon_l$$

To measure $\Delta_c$ by the proposed method and instrument, i.e. to use the instrument as a spectrodichrograph, we have:

a. To replace the analyzer in one of the beams of light with rotating polarization direction by the duly set Babinet-Soleil compensator which acts as an achromatic quarter-wave plate, and to shut off the second beam.

b. To place the substance under investigation into the said beam of light after the Babinet-Soleil compensator (the achromatic quarter-wave plate).

c. To measure the modulation coefficient of the electric signal generated in the photodetector by the said beam of light passed first through the compensator and then through the substance under investigation.

It is easy to show that the quarter-wave plate transforms the incident light with the rotating polarization direction into the light which can be described by the Stokes vector: [J; cos 2ωt; 0; −sin 2ωt]. The intensity of the transmitted beam of light remains constant, but its polarization state changes periodically from the left-hand circular polarization at $\omega t = 45°$ to the right-hand circular polarization at $\omega t = 135°$, passing through all the intermediate states of elliptical polarization, including the linear polarization at $\omega t = 0°$ and $\omega t = 90°$. This light can be regarded as a superposition of two light waves with the left-hand and the right-hand circular polarization, whose intensities are proportional to $\cos^2 \omega t$ and $\sin^2 \omega t$ respectively. When such light passes through a dichroic substance whose transmittency has different values $T_d$ and $T_l$ for the light right-hand and left-hand circularly polarized light, the intensity of the light transmitted by the substance, and therefore of the electric signal, is proportional to $$I = 1 + M \cos(2\omega t)$$

where the modulation coefficient $$M = \frac{T_l - T_d}{T_l + T_d}$$

Let C be the molar concentration of the substance in the sample and L the length of the way of light in it. Then $$M = \frac{\exp(-L.C. \epsilon_l) - \exp(-L.C. \epsilon_d)}{\exp(-L.C. \epsilon_l) + \exp(-L.C. \epsilon_d)} =$$

$$\tan h \left[ -\frac{L.C. \Delta_c}{2} \right] = \tan h \left[ \frac{\Delta_A}{2 \log e} \right]$$

The values of $\Delta_A$ are usually very small. Practically they don't exceed $10^{-3}$ to $10^{-2}$. We can therefore replace the hyperbolic tangent by its argument and compute $\Delta_c$ from $$M = \frac{L.C. \Delta_c}{2} = \frac{\Delta_A}{2 \log e}$$

5. Measurements of the linear dichroism

The linear dichroism of a substance can be characterized by the ratio of its minimal and maximal transmittency for the light linearly polarized in two orthogonal directions:

$$\Delta_l = (T_{min}/T_{max})$$

To measure the quantity $\Delta_l$ by the proposed method and instrument we have:

To let the beam of light with the rotating polarization direction to pass through the substance under investigation and to measure the modulation coefficient of the electric signal generated in the photodetector by the said beam of light.

Obviously, $$M = \frac{T_{max} - T_{min}}{T_{max} + T_{min}}$$

and $$\Delta_1 = \frac{1 - M}{1 + M} \quad (5)$$

6. Measurements of light scattering

The scattering of light by a substance can be characterized either by its turbidity T as defined by the Rayleigh equation:

$$\frac{J_{tr}}{J_o} e^{-T \cdot L}$$

or by its scattering coefficients $$S(\theta) = \frac{J(\theta)}{J_o}$$

which describe the spatial distribution of the light scattered by the substance.

Here $J_o$ is the intensity of the incident beam of light, $J_{tr}$ is the intensity of light transmitted by the substance and $J(\theta)$ is the intensity of light scattered at an angle $\theta$ to the direction of the incident beam of light.

The turbidity of a substance can be measured obviously exactly as the absorbency. To measure the scattering coefficients by the proposed method and instrument, i.e. to use the instrument as a spectronephelometer, we have:

a. To place a standard diffusor, whose coefficients of light scattering are known, into one of the beams I or II after the corresponding analyzer and to place the substance under investigation into the other beam;

b. To focus both the light scattered by the substance and the light scattered by the standard diffusor at a definite angle to the direction of the incident beam on the photodetector 8; a possible arrangement to do it is shown on FIG. 2;

c. To measure the phase of the electric signal generated in 8 against the reference signal produced in the detector 9 by the reflected part of the beam II.

If $\phi_1$ and $\phi_2$ are the values of the said phase differences measured with the substance under investigation being placed into the beam I or into the beam II respectively, then $$\frac{S(\theta)}{S(\theta)_{st}} = \left[ \frac{\tan \phi_1}{\tan \phi_2} \right]^{\frac{1}{2}} \tan \quad (6)$$

where $S(\theta)_{st}$ are the known scattering coefficients of the standard diffusor.

In the arrangement shown on the FIG. 2 the light is scattered by the substance under investigation and by the standard diffusor at angle $\theta = 90°$. It is clear that it is possible also to measure by the same way the scattering coefficients for any other values of $\theta$.

To investigate the scattering of the unpolarized light we have only to place the depolarizer (or a duly oriented quarter-wave plate) between the analyzer and the light scattering substance.

By putting duly oriented polarizers into the beams of scattered light one can investigate the state of polarization of the scattered light too.

It is clear that the above description is by way of example only and that it is possible to resort to various changes in the nature and arrangement of parts without departing from the scope and spirit of the present invention.

What is claimed is:

1. A method for measuring the values of quantities which characterize the optical properties of substances, including light absorption and scattering, circular and linear birefringence, circular and linear dichroism, which comprises:
   a. forming a beam of monochromatic linearly polarized light the polarization vector of which rotates at a predetermined frequency and the intensity of which does not depend upon the orientation of the polarization vector;
   b. measuring the phase of the electric signal produced in a photodetector by the said beam of light passed through a measuring path including the substance under investigation; or
   c. measuring the modulation coefficient of the electric signal produced in a photodetector by the said beam of light passed through a measuring path including the substance under investigation.

2. A method as claimed in claim 1 for measuring the absorbency and the transmittancy of substances, in which said beam-forming step includes the steps of:
   a. splitting the said beam of light into two partial beams of light with the same polarization properties;
   b. passing the said partial beams of light through at least one of two optical polarization analyzers oriented at an angle of 45° with each other and then through the substance under investigation and through a reference substance or a blank respectively;
   c. focusing both the said beams of light on the photodetector;
   and in which said measuring step includes the step of:
   d. measuring the phase of the resulting electric signal produced in the detector by the action of both the said beams of light and computing the values of the substance's absorbency or transmittency in response to said phase measurement.

3. A method as claimed in claim 1 for measuring a property selected from the properties of the light scattering coefficients and the turbidity of a substance, in which said beam-forming step includes the steps of:
   a. splitting the said beam of light into two partial beams of light with the same polarization properties;
   b. passing the said partial beams of light through at least one of two optical polarization analyzers oriented at an angle of 45° with each other and then respectively through the substance under investigation and through a standard diffusor, whose scattering coefficients are known;
   c. focusing the beams of light scattered under a definite angle by the substance under investigation and by the standard diffusor on a photodetector;
   and in which said measuring step includes the step of:
   d. measuring the phase of the resulting electric signal and computing the values of either or both the substance's scattering coefficients and its turbidity in response to said phase measurement.

4. A method as claimed in claim 1 for measuring circular birefringency (optical rotation) of a substance, in which said beam-forming step includes the steps of:
   a. passing the said beam of light first through the substance under investigation and then through an optical polarization analyzer;
   b. focusing the said beam of light passed through the substance and through the analyzer on a photodetector;
and in which said measuring step includes the step of:
   c. measuring the phase of the resulting electric signal produced in the detector in the presence of the substance in the beam of light and measuring the phase of the resulting electric signal in the absence of the substance in the beam of light and computing the value of the substance's circular birefringency in response to said phase measurements.

5. A method as claimed in claim 1 for measuring linear birefringency of an anisotropic substance, in which said beam-forming step includes the steps of:
   a. passing the said beam of light first through the substance under investigation and then through an optical polarization analyzer;
   b. focusing the said beam of light on the photodetector;
and in which said measuring step includes the step of:
   c. measuring the phase of the resulting electric signal produced in the detector in the presence of the substance in the beam of light at various orientations of the substance or the analyzer and measuring the phase of the resulting electric signal in the absence of the substance in the beam of light at various orientations of the analyzer and computing the value of the substance's linear birefringency in response to said phase measurements.

6. A method as claimed in claim 1 for measuring the circular dichroism of a substance, in which said beam-forming step includes the steps of:
   a. passing the said beam of light first through a quarter wave retarding plate, which can be represented by a duly set Babinet-Soleil compensator, and then through the substance under investigation;
   b. focusing the said beam of light on the photodetector;
and in which said measuring step includes the step of:
   c. measuring the modulation coefficient of the electric signal produced in the detector by the said beam of light passed through the quarter wave plate and the substance and computing the value of the substance's circular dichroism in response to said modulation coefficient measurement.

7. A method as claimed in claim 1 for measuring the linear dichroism of a substance, in which said beam-forming step includes the steps of:
   a. passing the said beam of light through the substance under investigation;
   b. focusing the said beam of light on a photodetector and in which said measuring step includes the step of:
   c. measuring the modulation coefficient of the electric signal produced in the detector by the said beam of light passed through the substance and computing the value of the substance's linear dichroism in response to said modulation coefficient measurement.

8. An apparatus for measuring a property selected from the properties of the absorbency and the transmittency of a substance, comprising: a source of light and a monochromator; a device to transform the monochromatic beam of light emerging from the monochromator into a beam of linearly polarized light, the polarization vector of which rotates with a predetermined frequency, but the intensity of which does not depend upon the direction of this vector; a device to split the said beam of light into two partial beams with the same polarization properties; two analyzers oriented at an angle of 45° with each other and placed each into one of the said partial beams of light; two photodetectors; a device to focus both the said partial beams of light after they have been passed through the substance under investigation and through the reference substance or a blank respectively on one of the said photodetectors; a device for measuring the phase of the electric signal produced in one photodetector by both the said beams of light against a reference signal, e.g. a signal produced in the other photodetector by a reflected part of one of the said beams of light passed through the corresponding analyzer.

9. An apparatus for measuring a property selected from the properties of the scattering coefficients and the turbidity of a substance, comprising: a source of light and a monochromator; a device to transform the monochromatic beam of light emerging from the monochromator into a beam of linearly polarized light, the polarization vector of which rotates with a predetermined frequency, but the intensity of which does not depend upon the direction of this vector; a device to split the said beam of light into two partial beams with the same polarization properties; two analyzers oriented at an angle of 45° with each other and placed each into one of the said partial beams of light; a photodetector; a device to focus both the said partial beams of light after they have been scattered at a definite angle to the direction of the incident beam by the substance under investigation and by a standard diffusor respectively on the said photodetector; a device for measuring the phase of the electric signal produced in the said detector by both the said beams of light against the reference signal.

10. An apparatus for measuring the circular birefringency (optical rotation) of a substance, comprising: a source of light and a monochromator; a device to transform the monochromatic beam of light emerging from the monochromator into a beam of linearly polarized light, the polarization vector of which rotates with a predetermined frequency, but the intensity of which does not depend upon the direction of this vector; a device to split the said beam of light into two partial beams with the same polarization properties; two optical polarization analyzers oriented at an angle of 45° with each other and placed each into one of the said partial beams of light; two photodetectors placed each into one of the said partial beams; a device to focus one of the said partial beams of light after it has been passed through the substance under investigation on one of the said photodetectors; a device to focus the other said partial beam on the other said detector; devices for measuring the phase of the electric signal produced in each of the said detectors by both the said beams of light; a device to compute the circular birefringency from the said phase measurements.

11. An apparatus for measuring the linear birefringency of a substance, comprising: a source of light and a monochromator; a device to transform the monochromatic beam of light emerging from the monochromator into a beam of linearly polarized light, the vector of polarization of which rotates with a predetermined frequency, but the intensity of which does not depend upon the orientation of this vector; an analyzer; a photoelectric detector; a device to focus the beam of light passed first through the substance under investigation and then through the analyzer on the detector; a device to turn the sample or the analyzer on various angles; a device to measure the phase of the electric signal produced in the detector by the said beam of light against a reference signal.

12. An apparatus for measuring the circular dichroism of a substance, comprising: a source of light and a monochromator; a device to transform the monochromatic beam of light emerging from the monochromator into a beam of linearly polarized light, the polarization vector of which does not depend upon the orientation of this vector; an achromatic quarter wave retardating plate or a Babinet-Soleil compensator which can act as such a plate; a photoelectric detector; a device to focus the said beam of light passed first through the quarter wave plate or the Babinet-Soleil compensator and then through the substance under investigation on the detector; a device to measure the modulation coefficient of the electric signal produced in the detector by the said beam of light.

13. An apparatus for measuring the linear dichroism of a substance, comprising: a source of light and a monochromator; a device to transform the monochromatic beam of light emerging from the monochromator into a beam of linearly polarized light, the polarization vector of which rotates with a predetermined frequency, but the intensity of which does not depend upon the orientation of this vector; a photoelectric detector; a device for measuring the modulation coefficient of the electric signal produced in the detector by the said beam of light passed through the substance under investigation.

14. An apparatus as claimed in any of claims 8, 9, 10, 11, 12 and 13 and further comprising optical filters to replace or to supplement the monochromator.

* * * * *

UNITED STATES PATENT AND TRADEMARK OFFICE
CERTIFICATE OF CORRECTION

PATENT NO. : 4,309,110

DATED : January 5, 1982

INVENTOR(S) : Leo Tumerman

It is certified that error appears in the above-identified patent and that said Letters Patent is hereby corrected as shown below:

Column 5, line 1, change "tg" to --tan--.

Column 9, line 41, change "after" to --after--.

Column 9, line 48, change "phase" to --phase--.

Column 9, line 60, change "$S(\theta)_{at}$" to --$S(\theta)_{st}$--.

Signed and Sealed this

Thirtieth Day of April 1985

[SEAL]

Attest:

DONALD J. QUIGG

Attesting Officer   Acting Commissioner of Patents and Trademarks